US008003046B2

(12) United States Patent  
Scheringer et al.

(10) Patent No.: US 8,003,046 B2  
(45) Date of Patent: Aug. 23, 2011

(54) DISINFECTION CONTROL BY TARGET PATHOGEN SELECTION

(75) Inventors: Stefan Scheringer, Offenburg (DE); Thomas Peukert, Oberkirch (DE); Markus Braun, Offenburg (DE)

(73) Assignee: MEIKO Maschinenbau GmbH & Co. KG, Offenburg (DE)

( * ) Notice: Subject to any disclaimer, the term of this patent is extended or adjusted under 35 U.S.C. 154(b) by 469 days.

(21) Appl. No.: 12/116,440

(22) Filed: May 7, 2008

(65) Prior Publication Data

US 2008/0283096 A1 Nov. 20, 2008

Related U.S. Application Data

(60) Provisional application No. 60/942,660, filed on Jun. 7, 2007.

(30) Foreign Application Priority Data

May 7, 2007 (DE) .......................... 10 2007 021 245

(51) Int. Cl.
| | |
|---|---|
| A61L 9/00 | (2006.01) |
| G01D 11/26 | (2006.01) |
| G01N 15/06 | (2006.01) |
| A61B 1/00 | (2006.01) |
| B08B 3/00 | (2006.01) |
| B08B 7/00 | (2006.01) |
| B08B 9/00 | (2006.01) |
| C12Q 1/68 | (2006.01) |

(52) U.S. Cl. ..................... 422/3; 422/1; 422/28; 422/32; 422/119; 422/68.1; 422/261; 422/292; 422/300; 134/26; 134/6; 134/18; 134/22.1; 134/56 R; 134/198; 435/6; 15/3.5; 600/133

(58) Field of Classification Search .................. 422/1, 3, 422/28, 32, 119, 68.1, 261, 292, 300; 134/26, 134/6, 18, 22.1, 56 R, 198; 435/6; 15/3.5; 600/133

See application file for complete search history.

(56) References Cited

U.S. PATENT DOCUMENTS

| 6,615,850 B1 | 9/2003 | Hornung | |
|---|---|---|---|
| 2005/0150527 A1* | 7/2005 | McKee et al. | ............... 134/57 D |
| 2007/0094303 A1* | 4/2007 | Zwingenberger et al. | . 707/104.1 |

* cited by examiner

Primary Examiner — Jill Warden  
Assistant Examiner — Monzer R Chornaji  
(74) Attorney, Agent, or Firm — Muncy, Geissler, Olds & Lowe, PLLC

(57) ABSTRACT

A method for operating a cleaning device or a cleaning system is proposed. In this case, the cleaning device is set up for carrying out a process for cleaning an article with a germicidal action. The method includes the following steps: information on a target germ with which the article could be contaminated is received; at least one process parameter of the cleaning process is selected according to the target germ in such a way that the target germ is killed with a high degree of probability during the cleaning process; and the cleaning process is carried out with the process parameter.

18 Claims, 2 Drawing Sheets

DISINFECTION CONTROL BY TARGET PATHOGEN SELECTION

This nonprovisional application claims priority to German Patent Application No. DE 102007021245, which was filed in Germany on May 7, 2007, and to U.S. Provisional Application No. 60/942,660, which was filed on Jun. 7, 2007, and which are both herein incorporated by reference.

BACKGROUND OF THE INVENTION

1. Field of the Invention

The invention relates to a method for controlling a cleaning appliance and to a cleaning system which is to be suitable particularly for carrying out the proposed method. The proposed method and the proposed cleaning system can be employed for cleaning a multiplicity of articles. A particular focus for the present application is the cleaning of nursing appliances and hospital appliances which are contaminated with a large quantity of liquid waste or other types of waste (for example, excretions, soiling, ointment residues, etc.), in particular basin washers for cleaning bedpans, basins, urine bottles or the like.

2. Description of the Background Art

Cleaning systems for a multiplicity of articles to be cleaned are known from many areas of daily life, industry, natural sciences and medicine or the nursing sector. As examples which, however, do not restrict the possible range of use of the present invention, dishwashers may be mentioned which are used, for example, in the industrial sector as single-chamber or multi-chamber dishwashers. As a further example, cleaning devices for medical appliances may be mentioned, in which large liquid quantities occur as waste, for example basin washers for cleaning basins, bedpans, urine bottles, nighttime utensils or similar containers from the medical sector or nursing sector. Here and hereafter, "liquid waste" is accordingly to be understood as also meaning quantities of other waste, such as, for example, human or animal excretions, ointment residues or similar waste.

Many cleaning devices serve to clean articles which come into contact directly or indirectly with the human body and therefore may serve as transmitters of diseases, in particular infections, and in which therefore particular importance is placed on sufficient disinfection or on achieving a known degree of hygiene.

Measuring and ensuring a degree of hygiene or germ reduction are the subject matter of numerous known methods and standards. Thus, in particular, the relationship between temperature and time on germ reduction is the basis for regulations and standards which are to ensure the cleaning action in dishwashers. On the basis of tests which were conducted on multi-tank dishwashers, with the aim of defining the process parameters with which reliable hygienic treatment of the batch is achieved, a method was developed for Germany, by DIN 10510 C3, which gives a recommendation as to temperature, cleaner concentration and duration between the first contact of the batch to be cleaned with the washing liquid of the first washing zone and the leaving of the rinsing-clear zone. With these recommended parameters, the multi-chamber dishwasher is then operated in the individual zones of the method in order to achieve the required germ reduction during operation. The basis for the standard mentioned is the germ reduction of test bodies, soiled in a defined way, after the cleaning process via what are known as mark-off investigations. The test germ or test organism used in this test is E-faecium ATCC 6057.

In the USA, the relationship between temperature and time on germ reduction is described by the NSF3 standard method. The basis for this stipulation is the germ reduction, determined from tests, of tuberculosis bacteria by the action of temperature over time. The action of temperature over time is in this case designated as the "heat equivalent". How many heat equivalents per second are achieved at which temperature is recorded in a table in this method. This table defines for dishwashers a minimum temperature for the washing water of the washing zone and of the rewashing zone which the dishwasher must reach in order to achieve the germ reduction required according to this standard.

U.S. Pat. No. 6,615,850 B1 discloses a method for operating a dishwasher, which comprises a continuous recording of the rewashing water temperature within the dishwasher and maintaining an optimal temperature. A cumulative heat equivalent (heat unit equivalent H.U.E.) is recorded, and the rewashing cycle is discontinued as soon as a stipulated H.U.E. value is reached.

According to the prior art, therefore, in conventional dishwashers and other cleaning devices a correspondingly preconfigured washing program is selected by the washing personnel. For example, an operator actuates corresponding keys and/or switches. Achieving the cleaning result and/or an envisaged germ reduction is assumed by means of appropriate parameterization for a very broad range of use and, if appropriate is confirmed in type tests and/or validations.

The known cleaning devices and cleaning methods, however, have the disadvantage that, as a rule, they function unspecifically with regard to the germs or pathogens actually present. Thus, for example, the batch is acted upon with a permanently stipulated thermal equivalent which, for example, can be selected so as to be sufficiently high to largely kill common pathogens or germs. As a rule, in this case, an "overkill" is adopted, since the estimated thermal equivalents, as a rule, are set high enough to kill all common types of germs. However, particularly in the area of industrial use with high batch throughputs, this entails high environmental pollution and an increased energy consumption, with the result that the operating costs and the environmental compatibility of cleaning devices of this type in many instances leave much to be desired. If, by contrast, the estimated thermal equivalent value is set too low, there is the risk that many germs are not killed and the batch may thus become a transmitter of infections.

SUMMARY OF THE INVENTION

It is therefore an object of the present invention to provide a method for operating a cleaning appliance, which, on the one hand, provides a reliable cleaning and disinfecting action and thus reduces the risk of a spread of infections, but, on the other hand, is environmentally friendly and can be implemented with reduced energy demand.

The basic idea of the present invention is to adjust cleaning in a directed manner to one or more types of known target germs. This takes into account the fact that, in many instances, information is available on what type of germs have contaminated the batch to be cleaned (also referred to hereafter as "article" or "batch"). Such information may originate from various sources, for example, in a hospital, from a prior diagnosis indicating the pathogen with which a specific patient who has previously used the article is infected. Other such information sources include regional, national or worldwide spreads of infections which may be provided, for example, by the Ministry of Health or by medical associations. There can also be an appropriate reaction to warnings of this kind.

This information on the target germ or target germs can then be utilized in order to adapt the cleaning process and/or the disinfection process in a directed manner to the target germ or target germs. Thus, without adopting an "overkill" which would neither be operationally efficient nor medically appropriate, the process (for example, with a minimum cleaning action being set) may be configured in such a way that all target germs are killed with a high degree of probability.

The proposed method may be applied to the operation of cleaning appliances of the most diverse possible types, for example of the types initially mentioned in the description of the prior at The particular focus of the proposed method is the cleaning of utensils and the cleaning of nursing appliances of the type initially mentioned. The cleaning appliance is to be set up in order to carry out a process for cleaning and/or disinfecting an article with a germicidal action.

The method has the steps mentioned hereafter, the sequence illustrated being preferred, but not mandatory, and individual steps being capable, for example, also of being carried out in parallel in terms of time, repeatedly or with a time overlap. Furthermore, even additional method steps not mentioned may be carried out.

First information on a target germ with which the article could be contaminated is received. This information may originate, for example, from one of the information sources described above and is preferably entered manually into the cleaning appliance by a user. However, other types of information reception may also be envisaged, for example reading in the information via an interface with a computer or computer network. Further details are explained below in connection with the cleaning system.

Subsequently, according to the target germ, at least one process parameter of the cleaning process is selected in such a way that the target germ is killed with a high degree of probability during the cleaning process. The process parameter may be for example, a temperature, a time of action of a cleaning step, a time of action of a thermal treatment step, a selection of a disinfectant or a quantity of a disinfectant. However, other process parameters, which have an influence on the cleaning or disinfecting action, as well as combinations of the process parameters mentioned or of other process parameters, may also be used.

Subsequently, the cleaning process is carried out with the process parameter or the process parameter set which was selected according to the target germ or target germs. If the cleaning process itself has a plurality of process steps, the previous steps, in particular the step of selecting a parameter set corresponding to the target germ, may also be carried out individually for each process step, for example separately for a circulation washing operation and a subsequent rewashing operation.

It is particularly preferred, in this case, if the information on the target germ is first utilized in order to select an experimental value of a target thermal equivalent corresponding to the target germ. This target thermal equivalent may, for example, be determined theoretically or else empirically by means of germicidal tests on various germs and constitutes the thermal equivalent at which the target germ is killed with a high degree of probability. For example, a minimum percentage of killed target germs may be stipulated for this purpose. The cleaning process can then be carried out in such a way that the article is acted upon at least with the target thermal equivalent.

In this case, again, it is preferable to use the thermal equivalents known from the various standards. For example, once again, thermal equivalents according to the EN ISO 15883 standard or the NSF3 standard may be used, in particular $A_o$ values and/or H.U.E. values. Other definitions of thermal equivalents may also be employed, which are based fundamentally on acting with thermal energy for a specific time upon the batch to be cleaned.

For example, the cleaning process may then be carried out in such a way that, in one or more treatment zones of a cleaning device, a temperature with which the article is acted upon is measured or monitored. Furthermore, a time of action in which the article is acted upon with the temperature may be measured so that thermal equivalents can thereby be calculated cumulatively. In this case, the various methods known partially from the prior art may be employed, such as, for example, the initially described method according to U.S. Pat. No. 6,615,850 B1, which is incorporated herein by reference, in which the temperature is monitored and the thermal equivalents are counted during rewashing in the washing chamber.

So that an assignment of one or more target germs to one or more process parameters can be carried out, with or without conversion into a target thermal equivalent value, various techniques known to a person skilled in the art may be employed. For example, appropriate databases, lists, tables, matrices, correlation curves or other assignments, which may be one-dimensional or multi-dimensional and which contain corresponding assignments, may be used. In this case, even a plurality of target germs may be combined into target germ groups or target germ classes with common or similar parameters. To ensure a minimum disinfecting action, it is possible, independently of the target pathogen which has been entered, to stipulate a minimum parameter set, which, for example, may be used when no target pathogen is known and/or is or is being read in.

In addition to the method described in one of the embodiments illustrated, furthermore, a cleaning system for cleaning an article is proposed, which is preferably set up so as to implement or use the method described in one of the embodiments illustrated. The cleaning system comprises at least one cleaning device which is set up for carrying out a process of cleaning the article with a germicidal action.

To receive the information on the target germ or target germs, the cleaning system may comprise, in particular, an input device which enables a user to enter the target germ. For example, a selection of known target germs for which there are corresponding parameter sets may be stipulated for a user. Should none of these target germs correspond to the user's stipulation, then, for example, a "default" value may be stipulated, for example the minimum parameter set described above. Even a plurality of minimum parameter sets are possible. The input device may comprise, for example, one or more displays (for example, a touch screen), a keypad, a mouse, a trackball or similar input devices known to a person skilled in the art. In particular, the input device may also comprise a computer with corresponding input and output means, for example a personal computer or a compact use-specific process control computer. Corresponding data stores and other elements usually arranged in computer systems may also be included. In particular, the input device may also comprise a wireless interface, for example an infrared or Bluetooth interface.

Alternatively or additionally to the proposed input device, the cleaning system may also comprise an interface for receiving information. For example, in this case, one or more of the abovementioned information sources on the target germs may be utilized. For this purpose, for example, the cleaning system may be connected to a corresponding network. The cleaning system may in this case also comprise a plurality of cleaning devices which can be controlled, for example, via a central control. For example, this central control may be set up in order to receive the information on the target germ centrally for all or a plurality of the cleaning devices.

Such a development of the invention can be manifested in a positive way, in particular, in hospitals or nursing homes or in other institutions with numerous cleaning devices which are preferably to be adapted synchronously to a specific target germ. For example, the central control may be arranged in a central technical monitoring station of a hospital or nursing home and, for example, may be supplied via a data transmission network, such as, for example, the internet, with information on the target germs to be expected. Alternatively or additionally, patient databases may also be connected to this central control and, for example, may deliver information that patients with a specific disease pattern or with specific infections are located in specific wards.

Correspondingly, the central control can then, for example, control cleaning devices which are known to clean articles which have come directly or indirectly into contact with the corresponding patients, in order to achieve the desired disinfecting or cleaning action for the target germs to be expected. The central control can again comprise one or more computers or computer networks which, for example, may again be equipped with corresponding input and output means, data stores and/or interfaces. In particular, the controls may be set up by programming, in order to control or carry out a method according to one of the design variants described above on one or more of the connected cleaning devices of the cleaning system.

If a central control of this type is used with a plurality of cleaning devices, one of the method variants described above can be manifested in a particularly positive way, to be precise the method variant of the assignment of target thermal equivalents. Thus, for example, the most diverse possible types of cleaning devices can be controlled centrally, without the device-specific process parameters having to be directly influenced centrally.

The assignment of target thermal equivalent to the stipulated target germ constitutes conversion into a common "currency" by means of which a large number of cleaning devices can operate independently of their exact function. Thus, at first, a target thermal equivalent may be assigned to the target germ in the central control. In this case, for example, once again, a list or another assignment of the type described above may be used. This assigned target thermal equivalent can then be transferred to the individual cleaning devices. Then, not until there, a cleaning process is carried out according to this target thermal equivalent stipulation, for example by means of corresponding controls, in such a way that the articles to be cleaned are acted upon with a target thermal equivalent. Thus, on the one hand, a reprogramming of each individual cleaning device is avoided, but at the same time the outlay in computing terms or the required resources for setting the optimal process parameters are distributed as beneficially as possible.

In addition to the dishwashers described above, in particular industrial dishwashers which may be designed as single-chamber or continuous-flow dishwashers, and to the likewise mentioned cleaning devices (also designated as cleaning and disinfecting appliances) for cleaning medical implements or nursing utensils with a high incidence of liquids, in particular basin washers for cleaning basins, urine bottles, bedpans, nighttime utensils, etc., the proposed cleaning system and the proposed method can also be used for a multiplicity of other types of articles or types of batches to be washed. In particular, here, mention must be made of cleaning devices for the disinfection of medical instruments without or with a low incidence of liquids, which can be used, for example, for surgical instruments or for dental instruments. In particular, these again may comprise thermal disinfection or sterilization devices (for example, an autoclave) and/or steam disinfection devices. Other types or articles, however, can also be cleaned.

Further details and features of the invention may be gathered from the following description of preferred exemplary embodiments in conjunction with the sub-claims. In this case, the respective features may be implemented by themselves or severally in combination with one another. The invention is not restricted to the exemplary embodiments.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
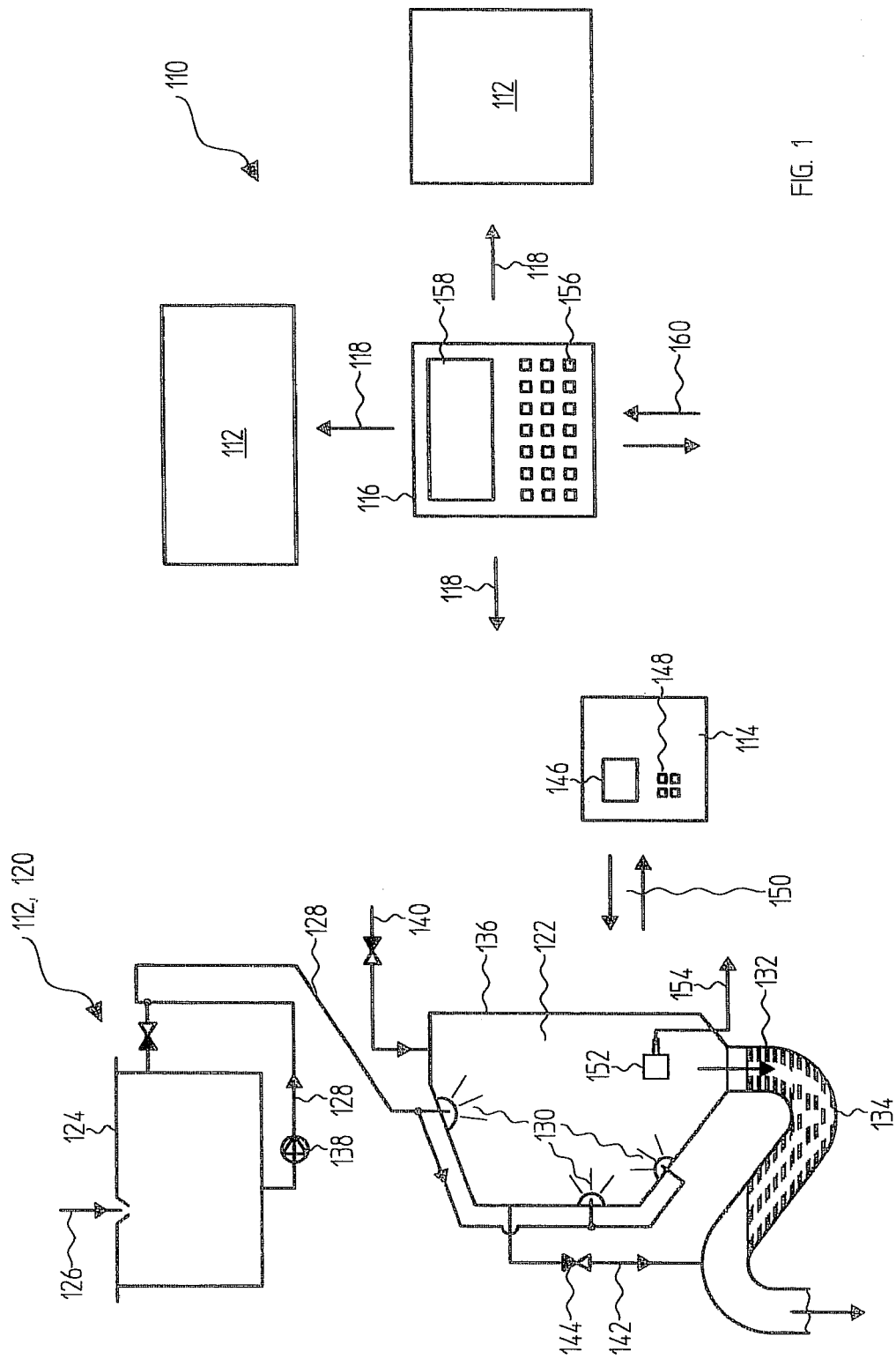
FIG. 1 shows a diagrammatical illustration of a cleaning system according to the invention.

FIG. 1 illustrates an exemplary embodiment of a cleaning system 110 according to the invention. In this exemplary embodiment, the cleaning system 110 comprises a plurality of cleaning devices 112 which, in part, are illustrated merely diagrammatically in FIG. 1. The cleaning devices 112 may, in particular, in each case comprise a specific control 114.

Furthermore, the cleaning system 110 has a central control 116 which, for example, can communicate with the controls 114 of the individual cleaning devices. This communication, which may be unidirectional or bidirectional, can take place, in particular, via a data connection designated in FIG. 1 by reference numeral 118.

Of the cleaning devices 112, only one cleaning device is illustrated in more detail, but still diagrammatically. This cleaning device 112 is a basin washer 120 which may be used for cleaning batches having a relatively high incidence of liquids (for example, basins, chamber pots, etc.) inside a washing chamber 122. The batch is in this case not illustrated in FIG. 1.

The basin washer 120 may be designed, for example, as is known from the prior art and as is described, for example, in DE 103 48 344 AI, which corresponds to U.S. Publication No. 20070104608, and which is incorporated herein by reference. Correspondingly, the basin washer 120 has, in addition to the washing chamber 122, a supply unit 124 which is connected to a water inflow 126 and which, for example, may comprise (not illustrated in FIG. 1) a water boiler and/or a steam generator. The supply unit 124 is connected to the washing chamber 122 via the feed lines 128 which, in particular issue in a plurality of nozzles 130 or orifices inside the washing chamber 122.

The washing chamber 122 has at its lower end an outflow 132 with a siphon bend 134 filled with a stock of liquid. After the batch has been introduced into the washing chamber 122 and the chamber doors 136 have been closed, the batch can then be emptied into the outflow 132 (for example, automatically by means of a pivoting movement) and can thus be freed roughly of its liquid waste. Subsequently, via the feed lines 128, action with cold or hot washing liquid (with or without additives, such as, for example, cleaning agents and/or disinfectants) can take place, thus bringing-about-rough washing or rough cleaning. To increase the pressure of the washing liquid, for example, a pump 138 may also be used. As a result, the batch can also be sprayed with a certain nozzle pressure out of the nozzles 130.

Even in this rough cleaning step, a certain disinfecting action can occur, for example in that washing liquid with an increased temperature (for example, a temperature of approximately 70 to 80° C.) is used, and/or in that disinfectants are admixed with the washing liquid. For example, for this purpose, the supply unit 124 may also comprise corresponding disinfectant tanks, in which case, for example, a suitable disinfectant can be selected from a plurality of available disinfectants or a disinfectant quantity can be adapted to a disinfecting action to be achieved. The time of action of the disinfectant on the batch also influences the disinfecting action. The time of action, the temperature and the disinfectant or washing agent quantity and the type of disinfectant or washing agent are examples of the controllable process parameters which influence the hygienic action and which as described hereafter can be selected according to one or more stipulated target germs.

After the liquid cleaning described, the batch can also be acted upon with steam and thereby further disinfected, likewise with the aid of the supply unit 124 containing the steam generator. Once again, for this purpose, the system of the feed line 128 and of the nozzles 130 may be used in order to carry out steam disinfection. In this case, in particular, the steam temperature and the time of action of the steam on the batch determine the cleaning and disinfecting action, so that these variables are further examples of possible process parameters which influence the hygienic action which can be selected according to the entered target germ or target germs.

After the steam disinfection, the steam can be displaced out of the inside of the washing chamber 122 by means of the forced introduction of supply air through an air feed line 140 and can be discharged into the outflow 132 via a discharge line 142, which has a nonreturn valve 144, with the siphon bend 134 being bypassed.

The cleaning process of the basin washer 120 can be monitored, controlled and/or regulated by means of the control 114. For example, the control 114 can act on the functions of the supply unit 124 in order to carry out the corresponding program steps in succession. The control 114 may, for example, be a control which is integrated into the basin washer 120 and which contains a display 146, operating elements 148 and a computer system with corresponding menu management. The control 114 can exchange information or commands with the remaining basin washer 120 via an interface 150.

Various monitoring and measuring devices may be provided for monitoring the cleaning action. In the present exemplary embodiment, the basin washer 120 comprises inside the washing chamber 122, at a location representative of the action upon the batch, at least one temperature sensor 152 which delivers information to the control 114 via a line 154.

It may be pointed out that the basin washer 120 illustrated in FIG. 1 constitutes only one possibility from a multiplicity of cleaning devices 112 in which the cleaning and disinfecting action or the germicidal action can be influenced by one or more parameters. In the present instance, these would be, for example, the abovementioned parameters, such as the quantity and/or type of a disinfectant or cleaning agent which is admixed as a liquid additive with the washing liquid, a time of action of the washing liquid composed in this way, the temperature of the washing liquid, the temperature and/or duration of steam disinfection, or similar parameters. In dishwashers or other types of cleaning devices 112, other parameters may correspondingly be relevant such as, for example, a belt speed which determines the dwell time of the batch in a treatment zone having an increased temperature.

Furthermore, time detection devices, for example conventional clocks and/or clock pulse generators of a processor, may also provided in the control 114 or at other locations of the cleaning device 112 or of the basin washer 120. These may be utilized, for example, in order, while at the same time taking into account the signals delivered by the temperature sensor 152, to determine thermal equivalents with which the batch has been acted upon within the washing chamber 122.

As described above, according to the exemplary embodiment in FIG. 1, the cleaning system 110 constitutes a decentralized cleaning system in which the central control 116 is separate from the controls 114 of the individual cleaning devices 112. An embodiment may just as well be envisaged, however, in which the cleaning system 110 comprises only a single cleaning device 112. In this instance, for example, the control 114 and the central control 116 may also be combined into one common control. A set-up may also be envisaged in which one of the cleaning devices 112 functions as a "master" and controls other cleaning devices 112 ("slaves"). In this instance, for example, the central control 116 may be combined with the control 114 of the master. Further architectures may be envisaged.

A possible flowchart of the method according to the invention will be described hereafter with reference to FIG. 2. For example, the central control 116 and/or the control 114 of the individual cleaning devices 112 in FIG. 1 can be set up by programming in order to carry out the method.

Figure 2:
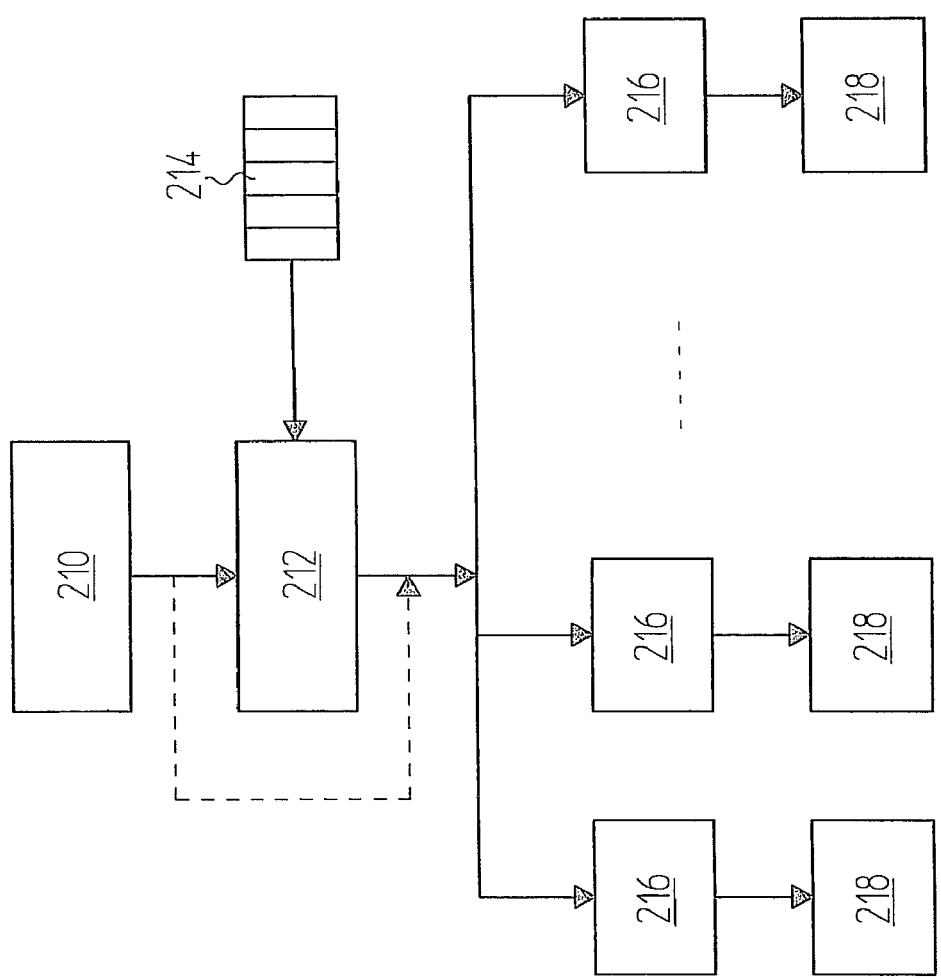
FIG. 2 shows a flowchart of an exemplary embodiment of a method according to the invention for operating the cleaning system according to FIG. 1.

In a first method step which is designated in FIG. 2 by 210, information on a target germ is received. For example, for this purpose, the central control 116 may again comprise operating elements 156 and a display 158, so that, for example, a user can select one or more target germs from a database or list (for example, by menu control). This may be carried out, for example, by a medical/technical assistant (MTA) in a hospital or by nursing personnel in a nursing home. A central control, for example, via a central computer operated by a hygiene officer, as a central control unit 116 in a hospital or as a central control unit 116 designed as a doctor's terminal, may also be envisaged.

Alternatively or additionally, the central control unit 116 may also have a wired or wireless data teletransmission device 160, for example a connection to the internet or a larger computer network. Information on the target germs to be killed may also be received via this.

Subsequently, in method step 212, in the exemplary embodiment, illustrated in FIG. 2, with the centralized control, the information on the target germ is converted into a corresponding target thermal equivalent. For this purpose, corresponding target thermal equivalents are read in, as designated symbolically in FIG. 2 by reference numeral 214. For example, this may involve a comparison of entered target germs with a table, as described above. For example, for this purpose an electronic table (for example, a lookup table) or a database may be provided.

If, instead of target thermal equivalents, information on the target germs is transferred directly to the individual cleaning devices 112, then method step 212 may even be bypassed, as illustrated by the broken line in FIG. 2. Both method variants are possible, or else combinations of the method variants described, in which both target thermal equivalents and "rough" information on the target germs to be expected are transferred to the individual cleaning devices 112 of the cleaning system 110. In the latter instance, for example, in the individual cleaning devices 112 a combined cleaning program may be carried out, in which, on the one hand, adherence to stipulated target thermal equivalents can be monitored and, on the other hand, other parameters can also be adjusted specially to the target germ, for example the type and/or metering and/or time of action of a disinfectant or the like.

The target thermal equivalents or the information on the target germs are then transferred to the individual cleaning devices 112. In these individual cleaning devices 112, suitable process parameters are then selected according to these stipulations, as designated in FIG. 2 by reference numeral 216. This selection may take place, for example, in the controls 114 of the cleaning devices 112. For example, once again, the information (information on the target germ and/or a target thermal equivalent) received from the central control 116 can be converted into suitable process parameters by comparison with a list, a table or a database. The process parameters are selected in such a way that they kill with a high degree of probability the target germ mentioned in method step 210.

In the event of target thermal equivalents being stipulated, this may be carried out, for example, in that, as process parameters, a temperature in the washing chamber 122 during a specific method step and also a specific dwell time within this temperature are stipulated. Even a simple accumulation of thermal equivalents is possible, in which case, for example, the cleaning process is discontinued as soon as the corresponding target thermal equivalent is reached.

Subsequently in method step 218, the cleaning process is carried out with the process parameters selected in each case in method step 216. As described above, this cleaning process may also be in multi-stage form, for example may comprise a plurality of program steps, so that, in particular, a plurality of process parameter sets can also be used for individual method steps.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for operating a cleaning device or a cleaning system, the cleaning device being set up for carrying out a process of cleaning an article with a germicidal action, the method comprising:
   receiving information on a target germ with which the article could be contaminated;
   selecting at least one process parameter of the cleaning process according to the identified target germ such that the target germ is killed with a high degree of probability during the cleaning process; and
   performing the cleaning process based, at least in part, on the selected process parameter,
   wherein a temperature with which the article is acted upon and a time of action in which the article is acted upon with the temperature is measured during the cleaning process, and
   wherein the information on the target germ is assigned an experimental value of a target thermal equivalent, corresponding to the target germ, at which the target germ is killed with a high degree of probability, wherein said selecting selects the at least one process parameter such that the cleaning process is carried out such that the article is acted upon at least with the target thermal equivalent.

2. The method according to claim 1, the at least one process parameter comprising at least one of the following parameters: a temperature; a time of action of a cleaning step with a cleaning liquid; a temperature of a cleaning liquid; a temperature of a thermal treatment step; a time of action of a thermal treatment step; a selection of a disinfectant; a type of a disinfectant; a quantity of a disinfectant; a time of action of a disinfectant; a steam temperature of a steam disinfection step; or a time of action of a steam disinfection step.

3. The method according to claim 1, wherein the target thermal equivalent corresponds to a thermal equivalent according to the EN ISO 15883 standard or to the NSF3 standard.

4. The method according to claim 1, wherein the target thermal equivalent comprises an Ao value and/or an H.U.E. value.

5. The method according to claim 1, wherein at least one of the temperature that is measured and/or the time of action that is measured is regulated or controlled.

6. The method according to claim 1, wherein an assignment of one or more target germs to one or more process parameters is used, and wherein the assignment comprises at least one of the following elements: a database; a list; a table; a matrix; or a correlation curve.

7. The method according to claim 1, wherein a plurality of target germs are combined into target germ groups or target germ classes with common parameters.

8. The method according to claim 1, wherein the target germ is selected according to a regional, national or worldwide frequency or frequency distribution of infections and/or epidemic warning and/or a medical diagnosis.

9. The method according to claim 1, wherein the cleaning process is carried, out, independently of the target pathogen, at least with a minimum parameter set for achieving a minimum germicidal action.

10. A cleaning system for cleaning an article, the cleaning system comprising:
   a cleaning device that is set up for carrying out a process of cleaning the article with a germicidal action,
   wherein the cleaning system is set up for receiving information identifying a target germ with which the article could be contaminated,
   wherein the cleaning system is set up for selecting at least one variable process parameter of the cleaning process according to the target germ such that the target germ is killed with a high degree of probability during the cleaning process, and
   wherein the cleaning system is set up for controlling the cleaning device to carry out the cleaning process based, at least in part, on the selected process parameter, and
   wherein the central control is set up for assigning a target thermal equivalent to the target germ or to the target germ class and for transferring information on the target thermal equivalent to the cleaning devices, the cleaning device being set up for carrying out in each case a cleaning process in such a way that the articles to be cleaned are acted upon with the target thermal equivalent.

11. The cleaning system according to claim 10, wherein the cleaning system further comprises an input device that enables a user to enter the information identifying a target germ or a target germ class, in particular to select a target germ or a target germ class from a target germ list or target germ class list.

12. The cleaning system according to claim 11, wherein the input device includes, means for displaying to the user at least one of a list of target germs or a list of target germ classes, and means for the user to select a target germ or a target germ class from the displayed target germ list or the displayed target germ dais list.

13. The cleaning system according to claim 10, wherein the cleaning system further comprises an interface in order to receive information on a regional, national or worldwide frequency or frequency distribution of infections, and/or an epidemic warning and/or information from a medical patient database.

14. The cleaning system according to claim 10, w wherein the cleaning system further comprises at least one of the following cleaning devices: a dishwasher, in particular an industrial dishwasher, in particular a single-chamber dishwasher or a continuous-flow dishwasher; a cleaning device for cleaning medical implements or nursing utensils with a high incidence of liquids, in particular a basin washer; or a cleaning device for the disinfection of medical instruments without or with a low incidence of liquids, in particular a thermal disinfection device, in particular an autoclave, and/or a steam disinfection device.

15. The cleaning system according to claim 14 wherein the cleaning device for cleaning medical implements or nursing utensils with a high incidence of liquids includes a basin washer for carrying out a basin washer cleaning process according to the selected process parameter.

16. The cleaning system according to claim 14 wherein the cleaning device for the disinfection of medical instruments without liquids or with a low incidence of liquids comprises a thermal disinfection device for carrying out a thermal disinfection process according to the selected process parameter.

17. The cleaning system of claim 16, wherein the thermal disinfection device includes at least one of an autoclave for carrying out an autoclaving cleaning according to the selected process parameter or a steam disinfection device for carrying out a steam disinfecting process according to the selected process parameter.

18. The cleaning system according to claim 10, wherein the cleaning system further comprises a plurality of cleaning devices and a central control, the central control being set up for receiving the information on the target germ centrally for the cleaning devices.

\* \* \* \* \*